United States Patent [19]

Updike

[11] Patent Number: 4,925,304
[45] Date of Patent: May 15, 1990

[54] SMALL BORE CERAMIC LASER TUBE INSPECTION LIGHT TABLE

[75] Inventor: Earl O. Updike, Tracy, Calif.

[73] Assignee: The United States of America as represented by the United States Department of Energy, Washington, D.C.

[21] Appl. No.: 292,149

[22] Filed: Dec. 30, 1988

[51] Int. Cl.⁵ .............................................. G01N 21/88
[52] U.S. Cl. .................... 356/237; 356/241; 356/426; 250/572
[58] Field of Search ............... 356/237, 339, 240, 241, 356/426, 428; 250/572

[56] References Cited

U.S. PATENT DOCUMENTS 3,418,482 12/1968 Masson ................................. 250/572
4,707,132 11/1987 Dutton ................................. 356/241

FOREIGN PATENT DOCUMENTS 0758850 10/1956 United Kingdom ................ 356/240

*Primary Examiner*—Vincent P. McGraw
*Assistant Examiner*—S. A. Turner
*Attorney, Agent, or Firm*—Miguel A. Valdes; Roger S. Gaither; William R. Moser

[57] ABSTRACT

Apparatus for inspecting small bore ceramic laser tubes, which includes a support base with one or more support rollers. A fluorescent light tube is inserted within the laser tube and the laser tube is supported by the support rollers so that a gap is maintained between the laser tube and the fluorescent tube to enable rotation of the laser tube. In operation, the ceramic tube is illuminated from the inside by the fluorescent tube to facilitate visual inspection. Centering the tube around the axial light of the fluorescent tube provides information about straightness and wall thickness of the laser tube itself.

6 Claims, 2 Drawing Sheets

SMALL BORE CERAMIC LASER TUBE INSPECTION LIGHT TABLE

FIELD OF THE INVENTION

The U.S. Government has rights in this invention pursuant to Contract No. W-7405-ENG-48 between the U.S. Department of Energy and the University of California for operation under Lawrence Livermore National Laboratory.

BACKGROUND OF THE INVENTION

The present invention relates to a light table apparatus to provide inspection capabilities for ceramic laser tubes, more particularly for small bore ceramic laser tubes.

The operation of small bore ceramic laser tubes is well known in the art. One aspect of the proper operation of such laser tubes is the uniformity and thickness of the interior of the laser tube itself. Such aspects are very critical in connection with proper operation of the laser. Information regarding the straightness and/or wall thickness of the laser tube can have dramatic influence on the frequency of operation, the amount of power delivered from the laser, and the like. Such information can be extremely critical in many applications.

In a laboratory environment such as at Lawrence Livermore National Laboratory in Livermore, Calif., the development of small bore lasers has been ongoing for experimental purposes. The operation of such lasers are used, for example, in an atomic vapor laser isotope separation (AVLIS) process. The operation of lasers in such an AVLIS process requires that the frequency and output power be maintained with extremely high accuracy. If the ceramic laser tubes for the lasers are not operating properly, this can have a dramatic and undesirable negative effect on the overall AVLIS process.

One approach for inspection of such ceramic laser tubes utilizes conventional light bulb suspended on a pole. One person pushes the light bulb down the ceramic tube to illuminate the inside. This would provide a basis of visually inspecting the laser tube itself for any contamination.

One significant problem with such an approach is the inability to uniformly provide visual inspection of the laser tube, because there is a large change in the lighting area surrounding the conventional light bulb, and shadows move along with the light.

It would be desirable, therefore, to provide an improved inspection apparatus for providing information about the interior of a small bore ceramic laser tube.

SUMMARY OF THE INVENTION

It is an object of the present invention to provide an improved light table apparatus for indicating visual information in connection with a small bore ceramic laser tube.

Briefly, the present invention provides an support base for a small bore laser tube which includes one or more support rollers.

The support base further includes a fluorescent light tube source which provides a means for illuminating the interior of the laser tube to permit visual inspection thereof.

In operation, the ceramic laser tube is placed over the fluorescent light tube, and the light tube is illuminated to facilitate visual inspection. Centering the laser tube around the axial light of the fluorescent tube provides information about the laser's straightness and wall thickness.

Other objects, features and advantages of the present invention will become apparent from the following detailed description and in part become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of this specification, illustrate an embodiment of the invention and, together with the description, serve to explain the principles of the invention.

DETAILED DESCRIPTION OF THE DRAWINGS

Reference will now be made in detail to a preferred embodiment of the invention, an example of which is illustrated in the accompanying drawings. While the invention will be described in conjunction with the preferred embodiment, it will be understood that it is not intended to limit the invention to that embodiment. On the contrary, it is intended to cover alternatives, modifications and equivalents as may be included within the spirit and scope of the invention as defined by the appended claims.

Figure 1:
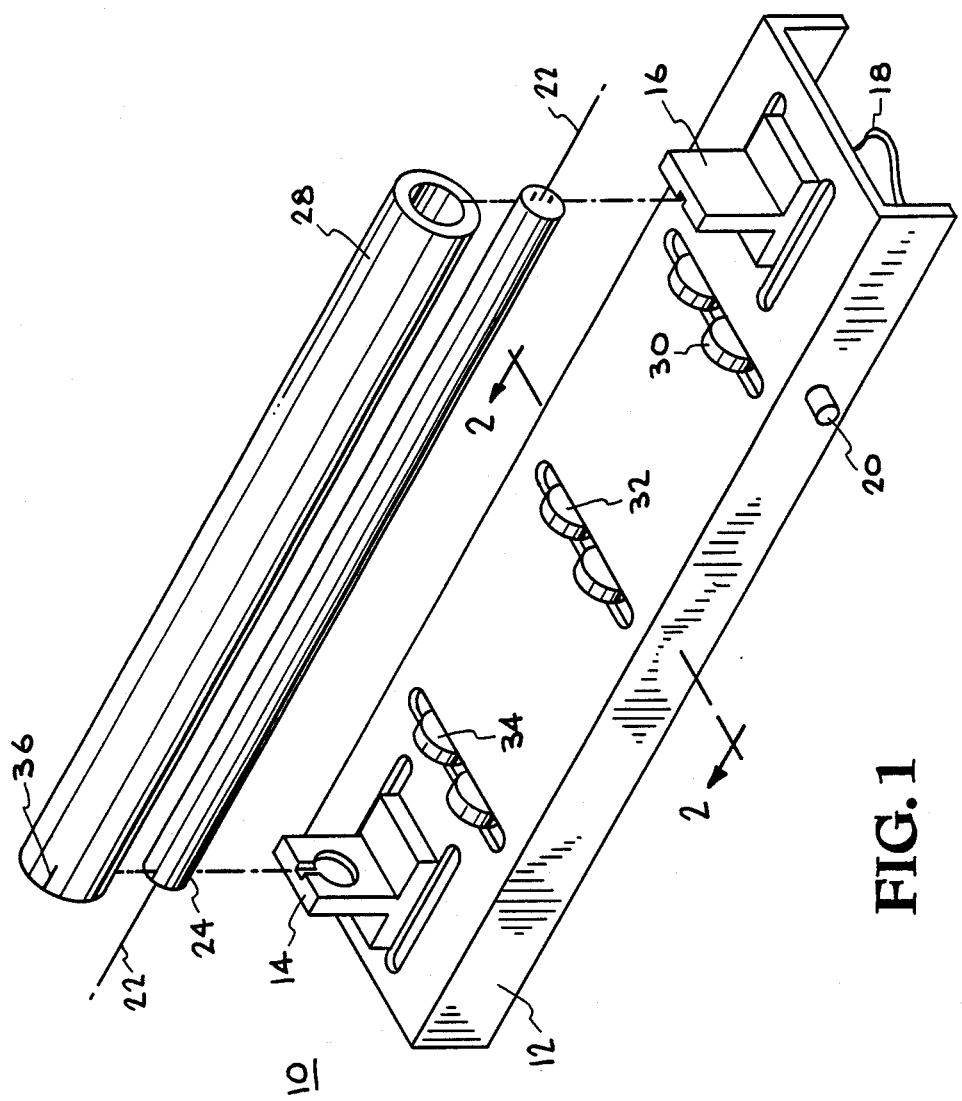
FIG. 1 depicts an exploded perspective view of the light table apparatus according to the present invention.

Referring now to FIG. 1, an exploded perspective view of a ceramic laser tube inspection light table 10 is depicted. The present invention provides a means of uniformly illuminating a ceramic laser tube 28 so as to provide for visual inspection ability of the laser tube itself for contaminants and the like.

The present invention, as depicted in FIG. 1, includes a support base 12 and two fluorescent light sockets 14, 16. Socket 14 is spring loaded compressible and socket 16 is stationary. The present invention further includes a fluorescent tube 24 and means for illuminating (on/off switch 20 and power line 18) fluorescent tube 24 when it is placed in electrical contact with the respective fluorescent light sockets 14, 16.

Figure 2:
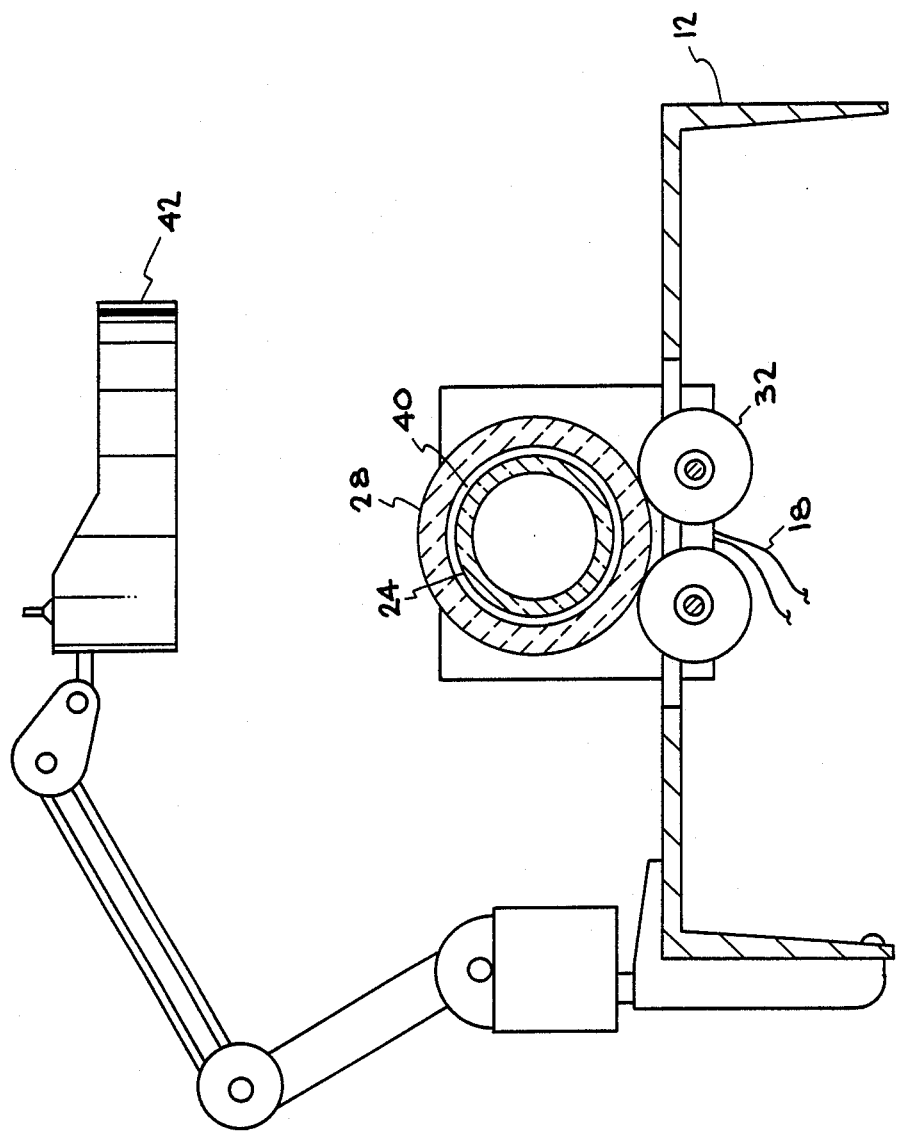
FIG. 2 depicts a cross-sectional view of the apparatus of FIG. 1.

The light table 10 further includes one or more support rollers 30, 32, 34, which can be adjusted, with suitable modification to Table 10, for predetermined heights depending on the size of the laser tube 28 which is undergoing inspection. In operation, a user will slide the fluorescent tube 24 within a ceramic tube 28 so as to leave a predetermined gap 40 (as seen in FIG. 2) between the interior wall of the ceramic laser tube 28 and the exterior wall of the fluorescent tube 24, for one reason that the fluorescent tube 24 would possibly be cut if it would come in contact with the ceramic tube 28.

The user then places the fluorescent tube 24 in an electrical connection with the fluorescent light sockets 14, 16 so that the fluorescent tube 24, when illuminated by on/off switch 20, will be stationary. The support rollers 30, 32, 34 will provide for rotational support of the laser tube 28 about the axis 22 of the fluorescent tube 24.

A user can make a hallmark 36 on one edge of the ceramic tube 28 and then incrementally rotate the ceramic tube 28 in increments of 45°, 90° or the like, and thereby provide a uniform visual inspection capability when the fluorescent tube 24 is suitably illuminated.

It has been found that, if there are defects in ceramic laser tube 28, a user of the present invention will see pinholes, cracks and the like. With respect to contamination of the walls, if a viewer sees a blue dot with a dark center with the visual inspection table, this could be an indication of cobalt contamination in the ceramic. If there is copper contamination, the viewer will see an orange-brown dot. With a reddish dot there is an indication of iron contamination.

In the inspection process, the interior of the laser tube 28 is illuminated with no background lighting. The fluorescent tube 24 is illuminated and the ceramic 28 tube can then be inspected visually. If the tube is in suitable operating condition, the user will see a yellowish-white type of illumination from the fluorescent tube 24 which is inside the ceramic tube 28. If there is a crack, the user will see light coming from the crack, or he will see a dark area that is like a pencil line over the area.

If contamination exists, the user will see colored spots, as mentioned above. With respect to a pinhole, the viewer will see a bright point of light coming out of the laser tube that is not discolored.

In further operation, the user can turn off the interior light of the fluorescent tube and illuminate the light table with an exterior light such as via a drafter's light fixture 42, as illustrated in FIG. 2.

The support rollers 30, 32, 34 of FIG. 1 provide for supporting and centering of the ceramic tube 28 around the axis 22 of the fluorescent tube 24, as well as provide for rotation of the ceramic laser tube 28 about the axis 22 of the fluorescent tube 24. This provides the capability of complete visual inspection of the ceramic tube 28 when rotated about the fluorescent tube 24. The centering is important in order to provide uniformity of the light from within the ceramic laser tube 28. The drafter's light 42, as illustrated in FIG. 2, is used for verification of any problems found during the inspection process.

In a laboratory environment such described above, the needs and requirements are generally far greater for proper laser operation than in private industry. As a result, there is a tendency to have much higher quality standards of materials and there is a need for special processes and equipment to insure the quality standards, such as proper inspection of a ceramic laser tube.

The foregoing description of a preferred embodiment of the invention has been presented for purpose of illustration and description. It is not intended to be exhaustive or to limit the invention to the precise form disclosed, and obviously many modifications and variations are possible in light of the above teaching.

The present embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for inspecting a ceramic laser tube comprising
   a support base,
   a fluorescent tube having a certain diameter which is less than the diameter of the laser tube to be inspected,
   means for providing visual inspection of said laser tube including
   means for inserting said fluorescent tube within said laser tube,
   a pair of electrical sockets located at the respective ends of said support base to provide for support of said laser tube and for illumination of said fluorescent tube,
   one or more rollers located on said support base for providing rotational support of said laser tube, including maintaining a uniform gap between the interior of said laser tube and the exterior of said fluorescent tube so that the illuminated laser tube can be rotated incrementally about the axis of said illuminated fluorescent tube.

2. The apparatus as in claim 1 further including an exterior light source means for exteriorly illuminating said laser tube.

3. The apparatus as in claim 1 wherein said support rollers are adjustable to provide for different sizes of laser tubes.

4. The apparatus as in claim 1 wherein said laser tube is a small bore laser tube.

5. The apparatus as in claim 1 wherein said laser tube is a large bore laser tube.

6. In an apparatus for visually inspecting a ceramic laser tube, the method comprising the steps of
   centering a fluorescent tube within said ceramic laser tube so as to maintain a gap between the exterior of said fluorescent tube and the interior of said ceramic laser tube,
   placing said fluorescent tube in a fixed position while permitting said ceramic laser tube to be rotated about the axis of said fluorescent tube,
   illuminating said fluorescent tube so as to illuminate said ceramic laser tube, and
   rotating said ceramic laser tube about said axis to provide a visual inspection capability.

* * * * *